United States Patent [19]

Hinata

[11] Patent Number: 5,617,204
[45] Date of Patent: Apr. 1, 1997

[54] METHOD FOR INSPECTING NECK PORTION OF MOLDED BOTTLE

[76] Inventor: Kunio Hinata, 665-1-126, Nobacho, Konan-ku, Yokohama, Kanagawa Prefecture, Japan

[21] Appl. No.: 425,058

[22] Filed: Apr. 19, 1995

[30] Foreign Application Priority Data

Apr. 19, 1994 [JP] Japan ................................. 6-104831

[51] Int. Cl.$^6$ ................................................. G01N 21/90
[52] U.S. Cl. ..................... 356/240; 250/223 B; 348/127
[58] Field of Search ................................. 356/240, 237, 356/394; 250/223 B; 348/125, 127, 129, 130

[56] References Cited

U.S. PATENT DOCUMENTS

| | | | |
|---|---|---|---|
| 4,498,003 | 2/1985 | Cibis | 356/240 |
| 4,606,635 | 8/1986 | Miyazawa et al. | 356/240 |
| 4,775,889 | 10/1988 | Yoshida | 356/240 |
| 4,811,251 | 3/1989 | Minato | 356/240 |
| 4,945,228 | 7/1990 | Juvinall et al. | 356/240 |

FOREIGN PATENT DOCUMENTS

| | | | |
|---|---|---|---|
| 0020650 | 2/1982 | Japan | 356/240 |
| 0065243 | 4/1984 | Japan | 356/240 |
| 60-193009 | 8/1986 | Japan . | |

*Primary Examiner*—Hoa Q. Pham
*Attorney, Agent, or Firm*—Townsend & Banta

[57] ABSTRACT

An inspection method for determining the presence and type of defects in the lip of a bottle. A CCD sensor and a light source are arranged at one side of the bottle above the lip, and additional light sources are arranged at the other side of the bottle above the lip. The presence and type of defects are determined by observing the profile of the image signal output by the CCD when light is reflected from the lip of the bottle. Defective bottles produce a wider than normal signal profile, two or more peaks, an interrupted profile or a weak arc image signal. The form of the image signal is indicative of the type of defect in the lip of the bottle.

9 Claims, 5 Drawing Sheets

METHOD FOR INSPECTING NECK PORTION OF MOLDED BOTTLE

BACKGROUND OF THE INVENTION

The present invention is directed to a method for inspecting the neck portion of containers such as bottles in a bottle manufacturing or filling line, particularly, the lip surface on the neck portion of a bottle. The invention more specifically concerns such a method which can readily be automated.

Conventionally, inspection of bottle lips was primarily carried out by visual inspection. However, it is impossible to accurately visually detect fine defects, and the productivity rate when visual inspection is employed is rather low.

To automate the inspection process, Japanese Examined Patent Publication No. Hei-5-40846 discloses an automated image sensor wherein light reflected from the entire area of the lip surface of the bottle is received by the sensor, and the resulting signal produced by the sensor is compared with a reference value. When the signal is greater than the reference value, the bottle is Judged as having a defect in the lip surface. When this occurs, the peak angle formed by the defect is determined from the ratio of the maximum depth of the defect to the width of the defect. When the angle is less than a certain value, the depth and width of the defect are calculated, and if the depth and width are greater than the reference value, the bottle is judged to be defective.

However, it is difficult to detect certain types of defects, for example, a dimple (FIG. 5(a)), an edge cut (FIG. 7(a)), or a blister or a line surface (FIG. 8(a)) etc., using the method disclosed in Japanese Examined Patent Publication No. Hei-5-40846 in cases where the depth and width of the defects are small. Further, since the method involves receiving light reflected from the entire area of the lip surface, it is necessary to obtain very stable light levels. Therefore, the conventional method has low reliability albeit at a high cost.

SUMMARY OF THE INVENTION

Overcoming the above drawbacks, the present invention provides a bottle inspection method which is capable of detecting defects which previously were difficult to detect, and which does so continuously, stably and at a low cost.

In order to achieve the above object, the present invention is directed to a method for detecting defects in the lip sealing surface of a bottle which is stopped at an inspection location and rotated by a rotating device the method comprising steps of:

providing a CCD image sensor arranged around the inspected bottle, providing light sources one of which is located on the same side of the neck of the bottle as the sensor and the others of which are located on the opposite side of the neck on right and/or left sides of the sensor, the CCD image sensor and the lighting sources being provided at an angle so as to look down toward the inside edge of the inspected neck region;

sensing a single reflected light beam with the CCD image sensor by sensing light reflected from the inside edge of the bottle, or a plurality of reflected light beams, by sensing light reflected from the inside edge of the neck over the entire area of the lip surface; and determining an inspected bottle to be defective when there is sensed a single reflected beam having a width greater than a specified threshold value width determined from a good bottle or if there are more than two reflected beams sensed.

The width of the reflected beam in the case of a good bottle (threshold value) can be set to allow a bottle to be temporarily Judged as defective, whereupon the bottle is rotated at the inspection location through different orientations, and the bottle finally judged defective if a reflected beam of increased width is continuously or repetitively detected.

The present invention is also directed to a method for detecting defects in the lip sealing surface of a bottle which is stopped at an inspection location and rotated by a rotating device, the method comprising steps of:

providing a CCD image sensor arranged around the inspected bottle, providing light sources one of which is located on the same side of the neck of the bottle as the sensor and the others of which are located on the opposite side of the neck on right and/or left sides of the sensor, the CCD image sensor and the lighting sources being provided at an angle so as to look down toward the inside edge of the inspected neck region;

sensing a reflected light beam with the CCD image sensor by sensing light reflected from the inside edge of the bottle; and determining an inspected bottle to be defective when there is sensed a reflected beam having a width greater than a specified threshold value width determined from a good bottle or if the reflected beam is weak or interrupted.

The defects which can be sensed with the invention include dimples, burrs, annular protrusions around the lip, depressions around the lip, lines in the lip surface, blisters, etc.

The image sensor, which may be either a one- or two-dimensional CCD array, is disposed at an angle of about 30° to 70° from horizontal, preferably 50° to 70°, and the light sources disposed at an angle of about 15° to 60° from horizontal, preferably 30° to 45°.

By properly arranging the CCD image sensor and light sources and by properly setting the lighting angle, the defect detection process can be performed well.

That is, a good bottle creates a single beam image or profile on the CCD image sensor, while a defective bottle creates a wider single beam image, multiple beam images, a weak image or an interrupted image on the sensor. The resulting image signals are analyzed and compared with a prestored signal produced from a good bottle. In accordance with the present invention, it is possible to effect Judgment as to the type of defect, such as dimples, burrs, annular protrusions around the inside of the lip, depressions around the lip, lines in the lip surface, blisters, etc., based on the form of the beam image signal obtained, i.e., by detecting the width, number, strength or continuity of the beam image signal.

It is also possible to inspect bottles of different shapes continuously and at a small cost by temporarily determining a bottle as defective, and then further inspecting the bottle while it is being rotated, finally rejecting it only when a signal indicative of a defective bottle is continuously detected.

DESCRIPTION OF THE PREFERRED EMBODIMENTS

Preferred embodiments of the present invention will now be described in detail with reference to the attached drawings.

Figure 2:
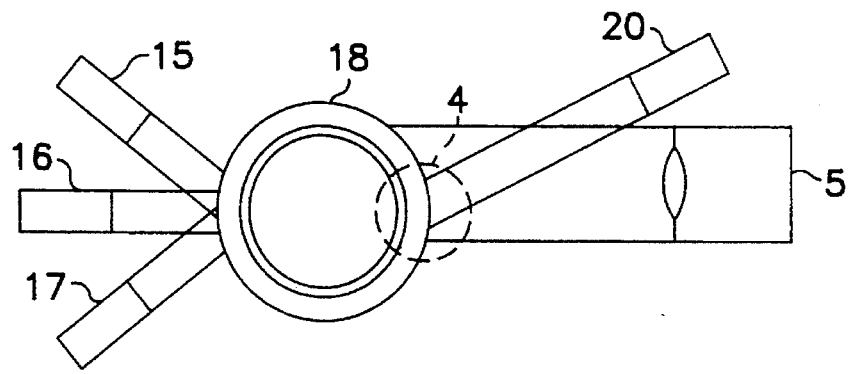
FIG. 2 is a plan view of an arrangement of an image sensor and light sources for practicing a preferred embodiment of the present invention.
Figure 3:
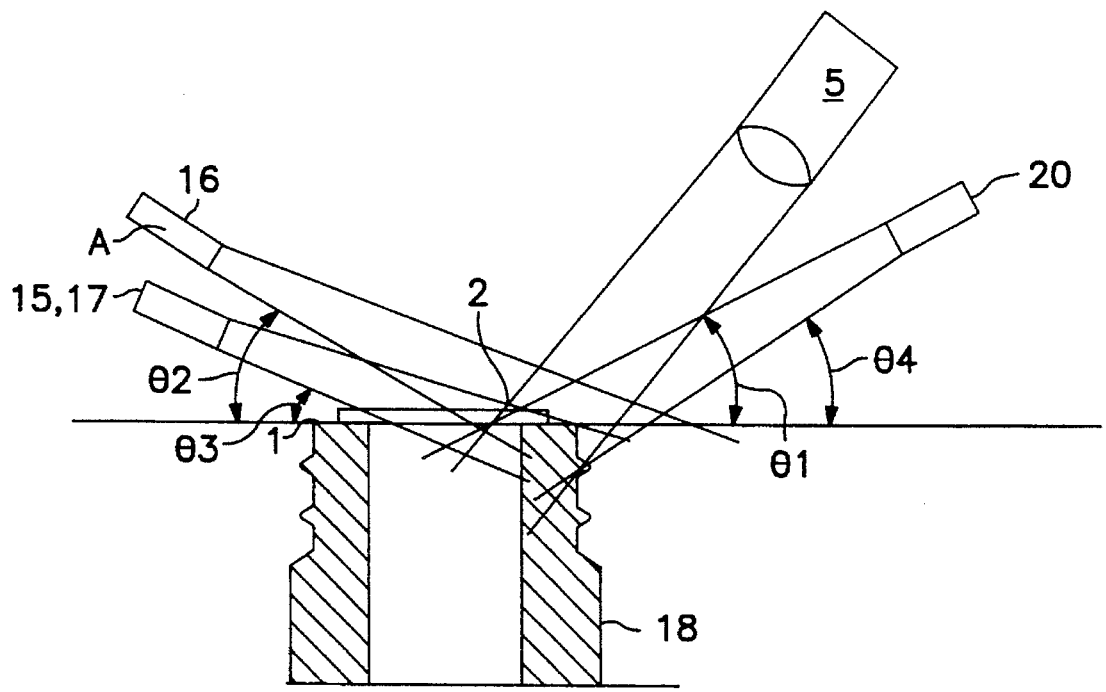
FIG. 3 is a side view illustrating another embodiment of the present invention.

FIGS. 2 and 3 show a bottle 18 and a light source 20 located on the same side of the bottle as a CCD sensor 5. A light source 16 is located on the opposite side of the sensor, and two additional light sources 15 and 17 are located on opposite sides of the light source 16, so that the light sources surround the bottle. The CCD sensor setting angle $\theta$ (i.e., the angle of the center optical axis of the CCD sensor) is about 50° to 70° from horizontal, preferably about 60°. The setting angle $\theta 2$ of the light source 16, the setting angle $\theta 3$ of the light sources 15 and 17, and the setting angle $\theta 4$ of the light source 20 are each about 30° to 45° from horizontal, preferably about 30°.

It is possible to use either a one- or two-dimensional sensor. However, in the case of a two-dimensional sensor it is necessary to narrow the image sensing area so that small movements of the bottle can be detected.

Figure 1:
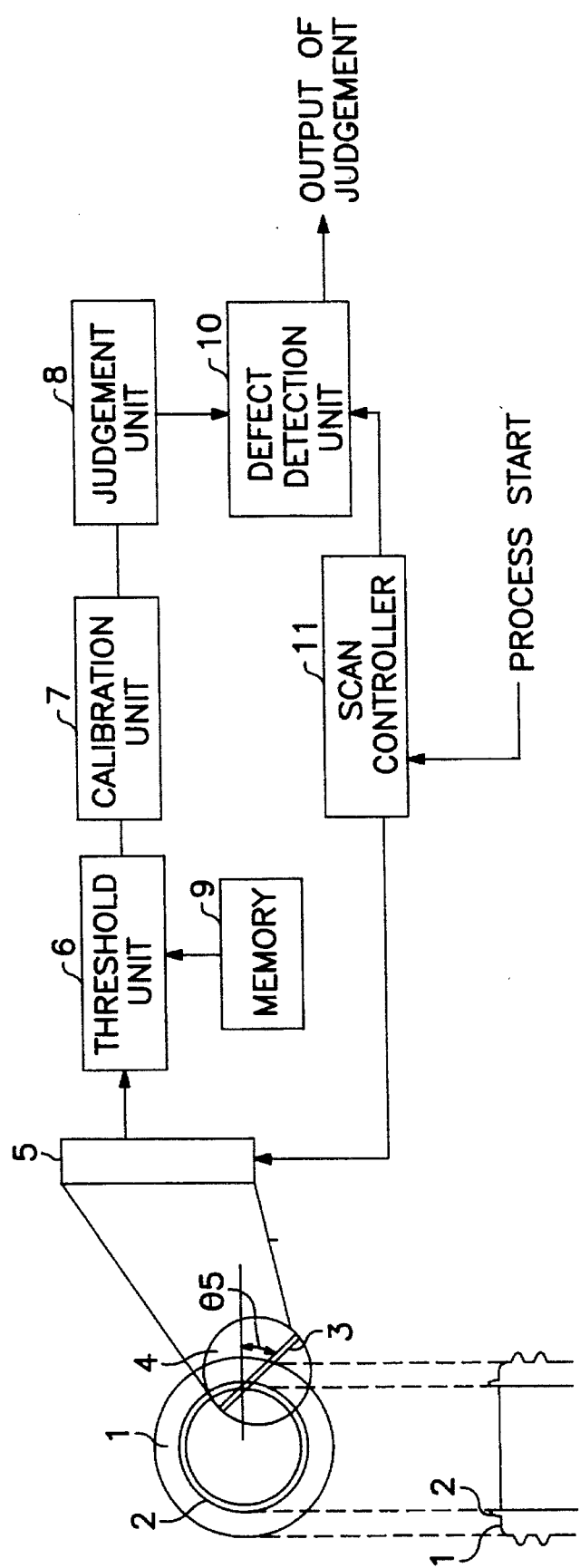
FIG. 1 is a block diagram illustrating an example of a bottle inspection method of the present invention.

As shown in FIG. 1, the CCD sensor 5 is set to scan in a scanning area 3 that extends at an angle $\theta 5$ of about 40° to 50° with respect to the radius of the bottle opening 2, preferably about 45°. The scanned surface produces an arc image signal or profile as shown in FIGS. 4(b), 5(b), 6(b), 7(b), 8(b) and 9(b).

The inspected bottle is conveyed and stopped at the inspection station as shown in FIGS. 2 and 3 by a bottle handling unit (not shown). The bottle is rotated at the station by a rotation device (not shown). The bottle is inspected and judged to be either good or defective while the bottle undergoes at least one revolution. Defective bottles are rejected from the line.

Examples of the inventive inspection method for different types of defects are illustrated in FIGS. 4(a), 5(a), 6(a), 7(a), 8(a) and 9(a). In these figures, for the sake of clarity, the positions of the CCD sensor 5 and light sources 15, 16, 17 and 20 are reversed from those shown in FIGS. 1 and 2.

Figure 4A:
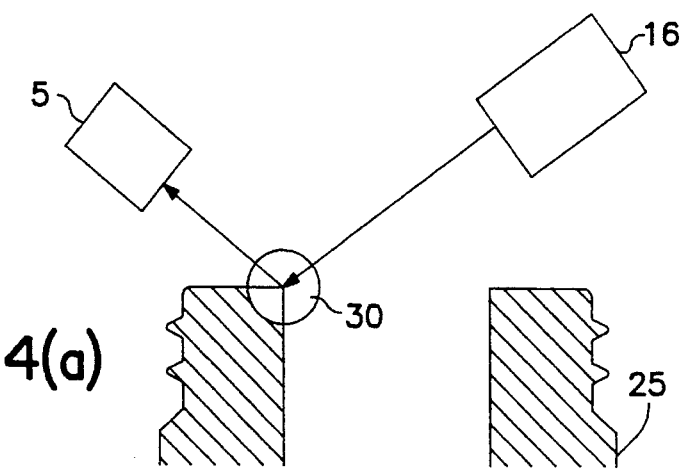
FIGS. 4(a) and 4(b) are respectively a schematic illustration showing a good bottle and the detected beam image signal produced thereby.
Figure 8A:
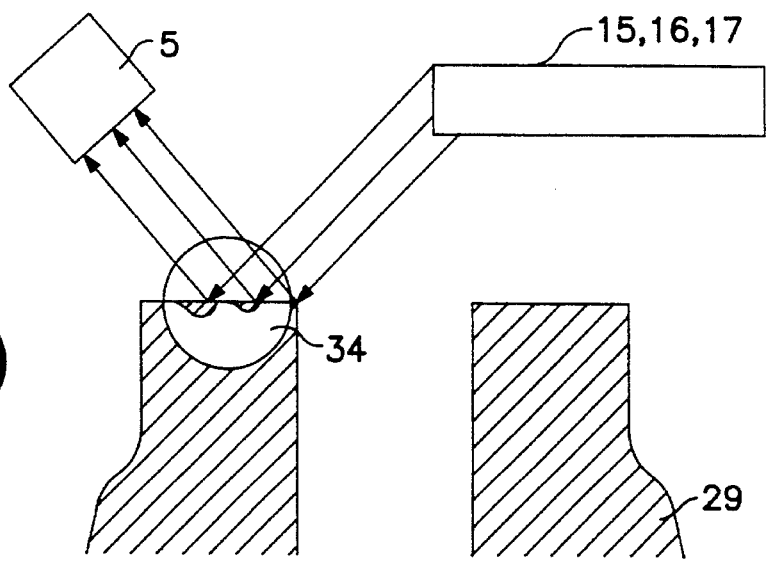
FIGS. 8(a) and 8(b) are respectively a schematic illustration showing another defective bottle having a blister on the lip thereof and the resulting detected beam image signal.

The light source 16 is arranged at an angle such that the CCD sensor 5 receives light reflected from the inside edge 30 of a good bottle 25, as shown in FIG. 4(a). Further, the light source 20 is arranged at an angle such that the CCD sensor 5 receives light reflected from the outside base of the neck 32, such as for the bottle 27 shown in FIG. 6(a). The light sources 15, 16 and 17 are arranged at angles so as to receive light reflected from a bottle 29 with a blister, burr, or line on its surface, as shown in FIG. 8(a).

The CCD sensor receives a sufficiently strong signal H2 from the area of the neck because the sensor is disposed so that the scanning area 3 extends at an angle $\theta 5$ with respect to the radial direction of the bottle, as shown in FIG. 1. For the case of a line or the like formed in the bottle surface, this angle $\theta 5$ allows a high scanning rate in the scanning area 3.

Figure 4B:
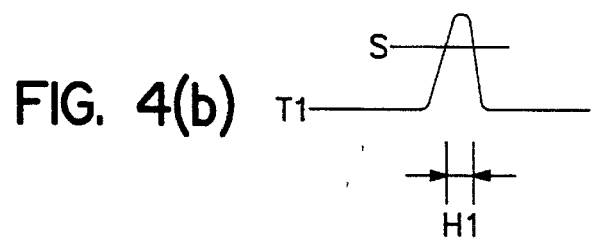

The light received in the scanning area 3 of the CCD sensor 5 is converted to an electric signal which exhibits a predetermined profile depending on the type of defect scanned by the sensor 5. In the case of the good bottle 25 as shown in FIG. 4(a) where the light source 16 is aimed at the inside edge 30 and the reflected light is received by the sensor 5, as shown in FIG. 4(b) the sensor outputs a signal T1 having a single well-defined pulse of width H1. In FIG. 1, S indicates a threshold level.

Figure 5A:
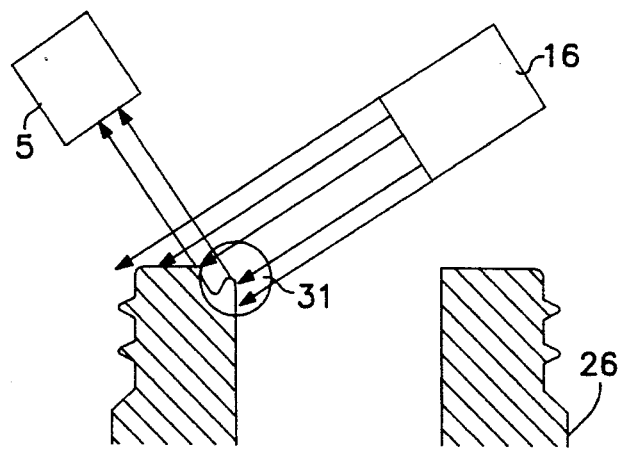
FIGS. 5(a) and 5(b) are respectively a schematic illustration showing a defective bottle having a dimple in the lip surface thereof and the resulting detected beam image signal.
Figure 5B:
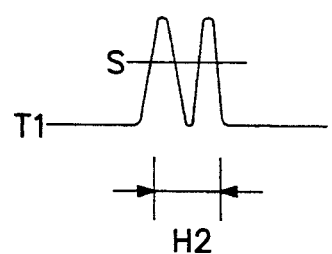

In a case where a dimple or depression is formed in the lip of the bottle 26 as shown in FIG. 5(a), when the light from the light source 16 strikes the inside edge 31 and returns to the sensor 5, as shown in FIG. 5(b) the sensor outputs a signal T2 exhibiting a double-pulse image profile having a total width H2, which is indicative of a defective bottle.

Figure 6A:
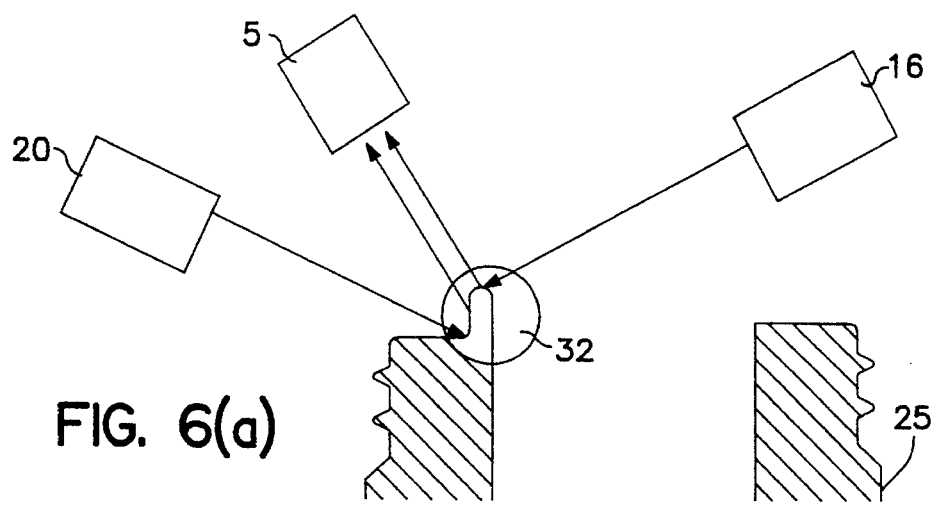
FIGS. 6(a) and 6(b) are respectively a schematic illustration showing another defective bottle having an annular protrusion around the inside of the lip and the resulting detected beam image signal.
Figure 6B:
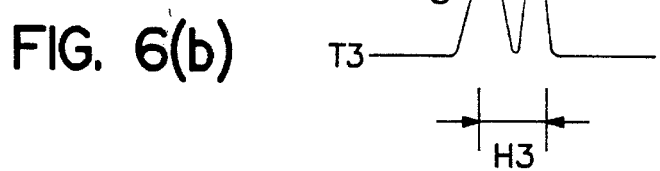

In the case of the bottle 27 shown in FIG. 6(a) having an unwanted annular protrusion around the inside of the lip, when the beams from the light sources 16 and 20 strike the inside edge 32 and return to the sensor 5, as shown in FIG. 6(b) the sensor outputs a signal T3 exhibiting a double-pulse image profile having a total width H2, which is indicative of a defective bottle.

Figure 7A:
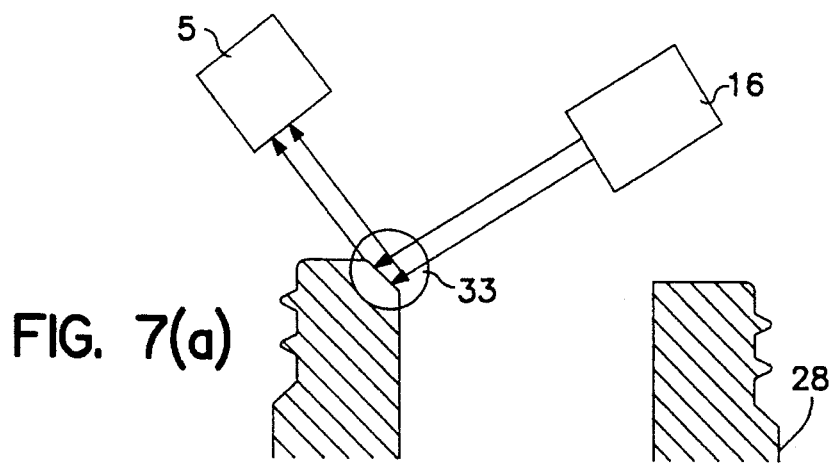
FIGS. 7(a) and 7(b) are respectively a schematic illustration showing another defective bottle having a depression around the inside edge of the lip and the resulting detected beam image signal.
Figure 7B:
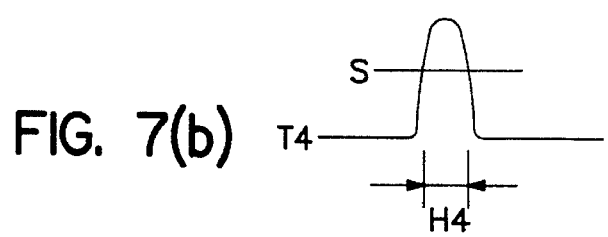

In a case where an unfilled portion occurs around the inside of the lip of the bottle 28 as shown in FIG. 7(a), when the light from the light source 16 strikes the inside edge 33 of the lip and returns to the sensor 5, as shown in FIG. 7(b), the sensor outputs a signal T4 having a wider pulse H4 than in the case of a good bottle, which is again indicative of a defective bottle, or at least a bottle which should temporarily be judged defective.

Figure 8B:
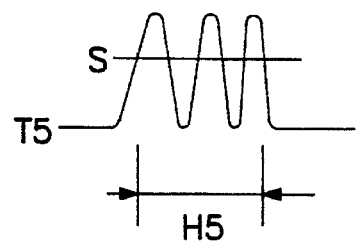

In case of a blister, mark or line on the surface of the bottle 29 as shown in FIG. 8(a), when the light beams from the light sources 15, 16 and 17 strike the inside edge 34 of the lip and return to the sensor 5, as shown in FIG. 8(b) the sensor outputs a signal T5 having a triple pulse image profile of width H5, which also is indicative of a defective bottle.

Figure 9A:
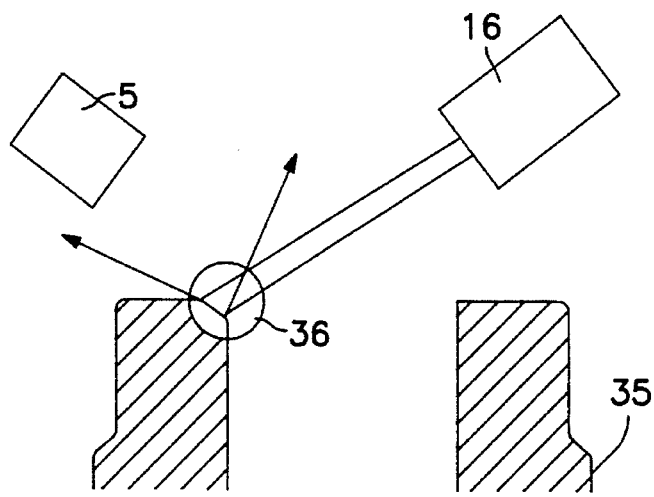
FIGS. 9(a) and 9(b) are respectively a schematic illustration showing another defective bottle having an unfilled portion along the inner edge of the lip thereof and the resulting detected beam image signal.
Figure 9B:
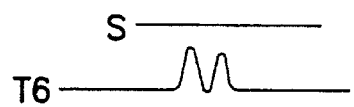

In the case illustrated in FIGS. 9(a) and 9(b), the light from the light source 16 strikes the inside edge 36 and is reflected thereby towards the sensor 5. As shown in FIG. 9(b), the sensor outputs a signal T6 having a double pulse image. However, because the pulses do not exceed the threshold, the case is judged indefinite.

The inventive inspection method will be explained below in more detail with reference to FIG. 1.

An analog signal T1 is output by the CCD sensor 5 for the good bottle sample 25, and compared by a threshold unit 6 with the preset threshold S which is set in advance and stored in a memory 9. The signal width H1 of the good sample 25 is calculated by a signal width determination unit 7 and the value H which is obtained by adding an allowance amount of the good sample to H1 is stored in a Judgment unit 8.

The threshold unit 6 is a binary calculation circuit which compares the threshold value S with, for example, an eight-bit digitized representation of the analog image signal data, and then judges values over the threshold as a "1" and values under the threshold as a "0".

For the image signal width determination, the width determination unit 7 searches for "1"s and "0"s in the output data from the threshold unit 6, counts the number of bits from the first "1" to the last "1", then determines this value as the signal width. In actual operation, the Judgment unit 8 compares the good reference width H and the width Hn output from the signal width determination unit 7.

For actual defect detection, it is preferable for the judgment unit 8 to add an allowance amount to the good reference width H1 and Judge a bottle to be good when the actual pulse width is lower than the allowance amount plus the good reference width (H), or defective when higher.

The scan controller 11 conducts scanning at a typical maximum rate of 0.3 mm/second.

The scan controller 11 signals the output unit to calibrate and synchronize the CCD sensor 5, the threshold unit 6, the signal width determination unit 7, the judgment unit 8, the threshold memory 9 and a defect detection unit 10.

It should be noted that it is desirable to start inspection only after the bottle is completely stopped at the inspection station.

In the inventive inspection method, the threshold S is set, for example, at a value of 30 in a case where the full range value is 255. This number is determined based on a typical reflected light brightness level to the sensor 5 of approximately 40 lux, a scanning rate on 0.3 mm/second, while using a 50 mm, F2.8 lens. Generally the value of H1 is the out put signal which is received from the CCD camera 5 and it indicates the width over the threshold "s", is about 20.

It should be noted that some fluctuation in the value of H1 for a good bottle may occur due to variations in the reflectivity of the lip surface, the rotation angle of the bottle, and the flatness of the lip surface. A value of about 30 where the number of pick up cells is 2048 may typically be used.

With the invention, it is possible to detect bottle defects continuously, automatically and at a low cost.

The invention is useful in accurately preventing defective bottles from being shipped from a plant.

What is claimed is:

1. A method for detecting a defect in a lip of a bottle, said method comprising the steps of:

positioning a CCD image sensor and a first light source located on the same side as the CCD image sensor, a second light source located on the opposite side of the CCD image sensor, a third light source located on the right side of the second light source, and a fourth light source located on the left side of the second light source, around a bottle to be inspected, said CCD image sensor and said first, second, third, and fourth light sources being disposed at an angle above the lip of the bottle looking down toward an inside edge of the lip;

energizing said light sources;

receiving on said image sensor light beams reflected from said lip energizing from the second light source for detecting a double pulse image profile, a wider single beam image, and a weak double pulse image, from both the second light source and the first light source for detecting a double-pulse image profile, and from the second, third and fourth light sources for detecting a triple-pulse image profile;

comparing a width and pulse of an output signal from said image sensor with a prestored reference value;

judging a bottle to be a defective bottle when said output signal has a width greater than said reference value or said output signal contains multiple pulses.

2. The method according to claim 1, further comprising the steps of temporarily judging a bottle to be defective when a width of said output signal exceeds said reference value, rotating the bottle temporarily judged as defective while continuously detecting said output signal, and judging said bottle as defective if said output signal continuously has a width greater than said reference value while said bottle is being rotated.

3. The method according to claim 1, wherein said bottle is additionally judged defective if said output signal is interrupted or is of a magnitude below a predetermined level.

4. The method according to claim 3, further comprising the step of determining a type of defect contained in said lip from a form of said output signal.

5. The method according to claim 3, wherein said CCD image sensor is positioned an angle of about 30° to about 70° from horizontal, and said first, second, third, and fourth light sources are positioned at angles of about 15° to about 60° from horizontal.

6. The method according to claim 3, wherein said CCD image sensor is positioned at an angle of about 50° to about 70° from horizontal, and said first, second, third, and fourth light sources are positioned at angles of about 30° to about 45° from horizontal.

7. The method according to claim 1, further comprising the step of determining a type of defect contained in said lip from a form of said output signal.

8. The method according to claim 1, wherein said CCD image sensor is positioned at an angle of about 30° to about 70° from horizontal, and said first, second, third, and fourth light sources are positioned at angles of about 15° to about 60° from horizontal.

9. The method according to claim 1, where said CCD image sensor is positioned at an angle of about 50° to about 70° from horizontal, and said first, second, third, and fourth light sources are positioned at angles of about 30° to about 45° from horizontal.

* * * * *